United States Patent
Masini

[19]

[11] Patent Number: 6,152,892
[45] Date of Patent: Nov. 28, 2000

[54] LIGHTWEIGHT CUSTOM-FITTED BODY PROTECTIVE DEVICE

[75] Inventor: Jon G. Masini, Highland, Mich.

[73] Assignee: Parker Athletic Products, LLC, Charlotte, N.C.

[21] Appl. No.: 09/376,253

[22] Filed: Aug. 18, 1999

[51] Int. Cl.[7] ....................................................... A61F 5/00
[52] U.S. Cl. .................................. 602/6; 602/8; 128/846
[58] Field of Search ................................... 602/6, 7, 8, 9; 128/846

[56] References Cited

U.S. PATENT DOCUMENTS

| | | |
|---|---|---|
| 1,689,558 | 10/1928 | Patten . |
| 2,553,612 | 5/1951 | Taylor . |
| 4,484,360 | 11/1984 | Leighton et al. . |
| 4,818,583 | 4/1989 | Geel . |
| 4,832,010 | 5/1989 | Lerman . |
| 5,364,580 | 11/1994 | Prent . |
| 5,454,780 | 10/1995 | Duback et al. . |
| 5,456,658 | 10/1995 | Duback et al. . |
| 5,544,663 | 8/1996 | Duback . |
| 5,755,678 | 5/1998 | Parker et al. . |

OTHER PUBLICATIONS

Author unknown, Firet Coremat® XX and XW, commerical literature, publication date was prior to the date this application was filed, 2 pages, publisher unknown.

Author unknown, Firet Coremat® XM, commerical literature, publication date was prior to the date this application was filed, 2 pages, publisher unknown.

Primary Examiner—Michael A. Brown
Assistant Examiner—Lalita Hamilton
Attorney, Agent, or Firm—Adams, Schwartz & Evans P.A.

[57] ABSTRACT

A custom-fitted athletic body protective product such as a shin guard, including a storage package formed of moisture-impervious material and sealable to prevent entry of moisture, a flexible protective guard positioned in the storage package and sealed therein against entry of moisture, and for being custom-formed to the shape of a body part to be protected while flexible and upon hardening providing a rigid, supporting custom fit to the body part. The protective product includes a low density core defining first and second major surfaces and first and second sheets positioned in overlying relation on respective first and second major surfaces of the core. The core and the first and second overlying sheet materials collectively defining a laminated substrate. A reactive system is impregnated into or coated onto the substrate, the reactive system remaining stable when maintained in substantially moisture-free conditions and hardening upon exposure to sufficient moisture to form a rigid, self-supporting structure of the substrate. A cover encloses the substrate.

30 Claims, 10 Drawing Sheets

LIGHTWEIGHT CUSTOM-FITTED BODY PROTECTIVE DEVICE

TECHNICAL FIELD AND BACKGROUND OF THE INVENTION

This invention relates to a custom-fitted, body protective guard, such as a shin guard, used to protect against injuries to sports participants, and to protect previous injuries from re-injury during continued play. The particular embodiment shown in the application is of a shin guard of the type to be used by soccer players during competition. The invention has application in any field—including non-sports related activities—which require, or make desirable, an accurate custom fit between the protective device and the body member. The invention takes advantage of polymer chemistry to permit quick and easy molding of a pad to the body part requiring protection. Shock attenuation is increased since the custom fit provides greater contact between the protective device and the body member.

Prior art body protectors include numerous types of guards which are fitted over the body part, such as the shin. These devices typically include a soft component to place near the skin and a hard, shell-like outer cover. The soft component is intended not only to provide a cushion, but also to accommodate itself to the varying configurations of differently sized and shaped body parts. For this reason, the cushioned part is substantially greater in thickness than required merely to provide the required amount of shock attenuation. Such devices are sufficiently "generic" that in many instances, they are required to be held in place by straps or bands.

Other prior art devices include pads which are constructed of thermosetting materials, which are heated and then formed to the body while heated. When cool, the pad retains the shape to which it was molded when heated. These products require a source of heat, and are susceptible to either over-or-under heating. In addition, body heat itself can soften or at least increase the flexibility of the pad, thereby decreasing the effectiveness of the protection offered by the pad. Some prior art pads include air bladders which provide an air cushion against injurious blows. Other prior art devices have a plurality of connected-together segments which are hinged for limited movement relative to each other, on the theory that such movement permits the pad to conform more closely to the body part. All of these prior art devices achieve only an approximation of a truly proper and anatomically correct fit.

The moisture curable resin system used in the present invention results in a very rigid pad, which holds the shape of the molded pad to a very high degree. No heat is required, and only a source of water is necessary. Atmospheric moisture alone will cure the pad into its hardened position in a relatively short period of time.

Shin guards, and other body protective guards cured into a hardened, custom-fitted shape with the use of moisture-curable resins, are disclosed in, for example, U.S. Pat. Nos. 5,456,658, 5,480,376 and 5,454,780, all owned by Parker Athletic Products, the assignee here. These patents disclose guards which represent significant progress in the development of lightweight, custom-formable guards for different parts of the body. In general, these guards are formed of a multi-layer woven or knitted fiberglass substrate, which is coated or impregnated with a moisture-curable resin, as described above. Padding and a front cover enclose the guard. Since their introduction several years ago, this type of guard has quickly become the best-selling product in the United States, and is now sold under not only the "Parker" trademark, but also the trademarks of several of the world's largest manufacturers of sports and athletic equipment.

Products according to the present invention represent a further step forward, in that it is even lighter in weight and thinner than earlier custom-formable shin guards without sacrificing strength, wear characteristics and protection. This is accomplished by utilizing a completely different substrate than that used in earlier products. Products made in accordance with the present invention can be quickly and easily applied to a body part in such a way as to achieve a true custom fit. This new shin guard requires less resin than prior art Parker guards, while maintaining all of the desirable characteristics of those guards.

SUMMARY OF THE INVENTION

Therefore, it is an object of the invention to provide a body protective guard and guard product which can be molded to fit the body part requiring protection, as described below.

It is another object of the invention to provide a body protective guard which hardens in the presence of moisture to form a very rigid, but very lightweight protective structure.

It is another object of the invention to provide a body protective guard which provides protection to the skeletal structure of the wearer, including bones which lie close to the skin.

It is another object of the invention to provide a body protective guard which is suitable for protecting bones lying close to the skin against injury, and protecting injured bones against further damage.

It is another object of the invention to provide a body protective guard which can be worn without being held in place by straps or belts.

It is another object of the invention to provide a body protective guard which uses less resin to form the hardenable substrate.

It is another object of the invention to provide a body protective guard which is very thin and easily conformable to the body part to be protected.

It is another object of the invention to provide a body protective guard which can be molded to a small bending radius without loss of strength or capacity to protect the body part.

It is another object of the invention to provide a shin guard which provides the above-identified attributes and objects.

These and other objects of the present invention, are achieved in the preferred embodiments disclosed below by providing a custom-fitted athletic body protective product, comprising a storage package formed of moisture-impervious material and sealable to prevent entry of moisture, a flexible protective guard positioned in the storage package and sealed therein against entry of moisture, for being custom-formed to the shape of a body part to be protected while flexible upon hardening, providing a rigid, supporting custom fit to the body part. The protective product comprises a low density core defining first and second major surfaces and first and second sheets positioned in overlying relation on respective first and second major surfaces of the core. The core and the first and second overlying sheet materials collectively define a laminated substrate. A reactive system is impregnated into or coated onto the substrate, the reactive system remaining stable when maintained in substantially moisture-free conditions and hardening upon exposure to sufficient moisture to form a rigid, self-supporting structure of the substrate. A cover encloses the substrate.

According to one preferred embodiment of the invention, the cover includes a flexible protective pad positioned on one side of the substrate along its length to provide a cushioning barrier between the hardened substrate and the protected body part.

According to another preferred embodiment of the invention, the cover includes a fabric material enclosing the substrate on a side opposite the flexible protective pad.

Preferably, the core comprises a random, non-continuous polyester non-woven fabric.

According to yet another preferred embodiment of the invention, the core comprises a random, non-continuous polyester non-woven fabric having a filler comprised of microspheres.

According to yet another preferred embodiment of the invention, the core is comprises a random, non-continuous polyester non-woven fabric filled with microspheres at least 50 percent by volume.

According to yet another preferred embodiment of the invention, the core comprises a random, non-continuous polyester non-woven fabric filled with microspheres at least 60 percent by volume.

According to yet another preferred embodiment of the invention, the core comprisesf a low density, non-woven, continuous strand fabric.

According to yet another preferred embodiment of the invention, the microspheres are plastic, and the core includes a styrene-soluble binder.

According to yet another preferred embodiment of the invention, the core is between 2 mm (0.0787 in.) and 3 mm (0.1181 in. thick).

According to yet another preferred embodiment of the invention, the flexible protective pad comprises foam.

A custom-fitted athletic body protective guard according to another embodiment of the invention comprises a flexible protective guard and for being custom-formed to the shape of a body part to be protected, while flexible and upon hardening providing a rigid, supporting custom fit to the body part. The protective guard comprises a low density core defining first and second major surfaces, first and second sheets positioned in overlying relation on respective first and second major surfaces of the core, the core and the first and second overlying sheet materials collectively defining a laminated substrate. A reactive system is impregnated into, or coated onto the substrate, the system remaining stable when maintained in substantially moisture-free conditions and hardening upon exposure to sufficient moisture to form a rigid, self-supporting structure of the substrate. A cover encloses the substrate.

According to yet another preferred embodiment of the invention, the cover includes a flexible protective pad positioned on one side of the substrate along its length, to provide a cushioning barrier between the hardened substrate and the protected body part.

According to yet another preferred embodiment of the invention, the cover includes a sheet material enclosing the substrate on a side opposite the flexible protective pad.

According to yet another preferred embodiment of the invention, the core comprises a random, non-continuous polyester non-woven fabric.

According to yet another preferred embodiment of the invention, the core comprises a random, non-continuous polyester non-woven fabric having a filler comprising microspheres.

According to yet another preferred embodiment of the invention, the core comprises a random, non-continuous polyester non-woven fabric filled with microspheres at least 50 percent by volume.

According to yet another preferred embodiment of the invention, the core comprises a random, non-continuous polyester non-woven fabric filled with microspheres at least 60 percent by volume.

According to yet another preferred embodiment of the invention, the core comprises a low density, non-woven, continuous strand fabric.

According to yet another preferred embodiment of the invention, the microspheres are plastic, and the core includes a styrene-soluble binder.

According to yet another preferred embodiment of the invention, the core is between 2 mm (0.0787 in.) and 3 mm (0.1181 in.) thick.

According to yet another preferred embodiment of the invention, a flexible protective pad is comprised of foam.

According to yet another preferred embodiment of the invention, a custom-fitted protective shin guard is provided, comprising a storage package formed of moisture-impervious material and sealable to prevent entry of moisture, a flexible protective shin guard positioned in the storage package and sealed therein against entry of moisture, and for being custom-formed to the shin to be protected while flexible and upon hardening providing a rigid, supporting custom fit to the shin. The shin guard comprises a low density core defining first and second major surfaces and first and second sheets positioned in overlying relation on respective first and second major surfaces of the core, the core and the first and second overlying sheet materials collectively defining a laminated substrate. A reactive system is impregnated into, or coated onto the substrate, the system remaining stable when maintained in substantially moisture-free conditions and hardening upon exposure to sufficient moisture to form a rigid, self-supporting structure of the substrate. A cover encloses the substrate. The cover includes a flexible protective pad positioned on one side of the substrate along its length, to provide a cushioning barrier between the hardened substrate and the protected body part.

According to another preferred embodiment of the invention, the cover includes a sheet material enclosing the substrate on a side opposite the flexible protective pad.

According to yet another preferred embodiment of the invention, the core comprises a random non-continuous, polyester non-woven fabric filled with microspheres at least 50 percent by volume.

According to yet another preferred embodiment of the invention: a substrate structure for a custom-fitted athletic body protective product, comprises a storage package formed of moisture-impervious material and sealable to prevent entry of moisture, a substrate structure for being packaged in a moisture-impervious storage package and sealed therein against entry of moisture, and for being custom-formed to the shape of a body part to be protected while flexible and upon hardening providing a rigid, supporting custom fit to the body part, the substrate structure comprising a low density core defining first and second major surfaces, the low density core including a random laid, non-continuous polyester non-woven fabric filled at least 50% by volume with microspheres. At least one sheet is positioned in overlying relation, on a respective one of the first and second major surfaces of the core. The core, and the at least one sheet collectively define a laminated substrate for the shin guard. A reactive system is impregnated into, or coated onto the substrate, the system remaining stable when maintained in substantially moisture-free conditions and hardening upon exposure to sufficient moisture to form a rigid, self-supporting structure of the substrate.

According to another preferred embodiment of the invention, a cover is provided for enclosing the substrate, and includes a flexible protective pad positioned on one side of the substrate along its length to provide a cushioning barrier between the hardened substrate and the protected body part.

According to yet another preferred embodiment of the invention, the cover includes a fabric material enclosing the substrate on a side opposite the flexible protective pad.

According to yet another preferred embodiment of the invention, the core comprises a random, non-continuous polyester non-woven fabric.

BRIEF DESCRIPTION OF THE DRAWINGS

Some of the objects of the invention have been set forth above. Other objects and advantages of the invention will appear as the invention proceeds, when taken in conjunction with the following drawings, in which.

DESCRIPTION OF THE PREFERRED EMBODIMENT AND BEST MODE

Figure 1:
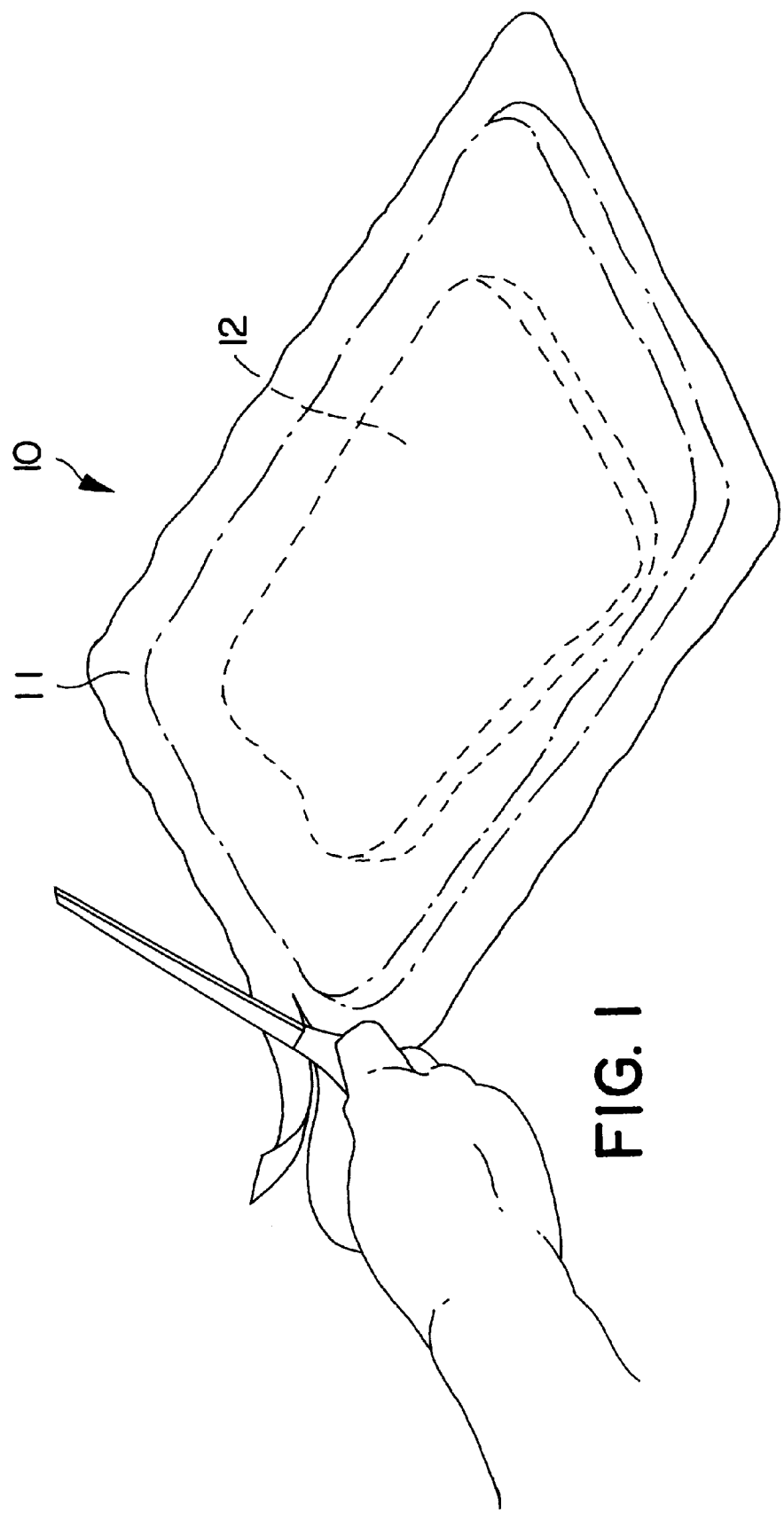
FIG. 1 is a perspective view of a shin guard product according to an embodiment of the invention being opened prior to removing the shin guard from its protective envelope.

Referring now specifically to the drawings, FIG. 1 illustrates an athletic body protective product 10 is shown according to an embodiment of the invention. The particular body protective product described for purposes of illustration is a shin guard. The body protective product 10 includes as its outermost protective enclosure, an outer moisture-impervious laminated foil pouch 11 in which the other components are sealed in the absence of moisture. The preferred structure of the outer moisture-impervious pouch 11 is preferably a 0.0013 cm. (0.5 mil) aluminum foil sheet sandwiched between two layers of low density polyethylene film, each layer having a thickness of 0.0051 cm. (2 mils). Additionally, the pouch 11 can include an outer layer of laminated 60 gauge bi-axially oriented nylon film. This laminate structure, when properly formed into an envelope and sealed, will prevent moisture intrusion indefinitely. The pouch 11 contains a protective guard according to the invention. For purposes of illustration in this application, the body protective guard is a shin guard 12, as described below.

Figure 2:
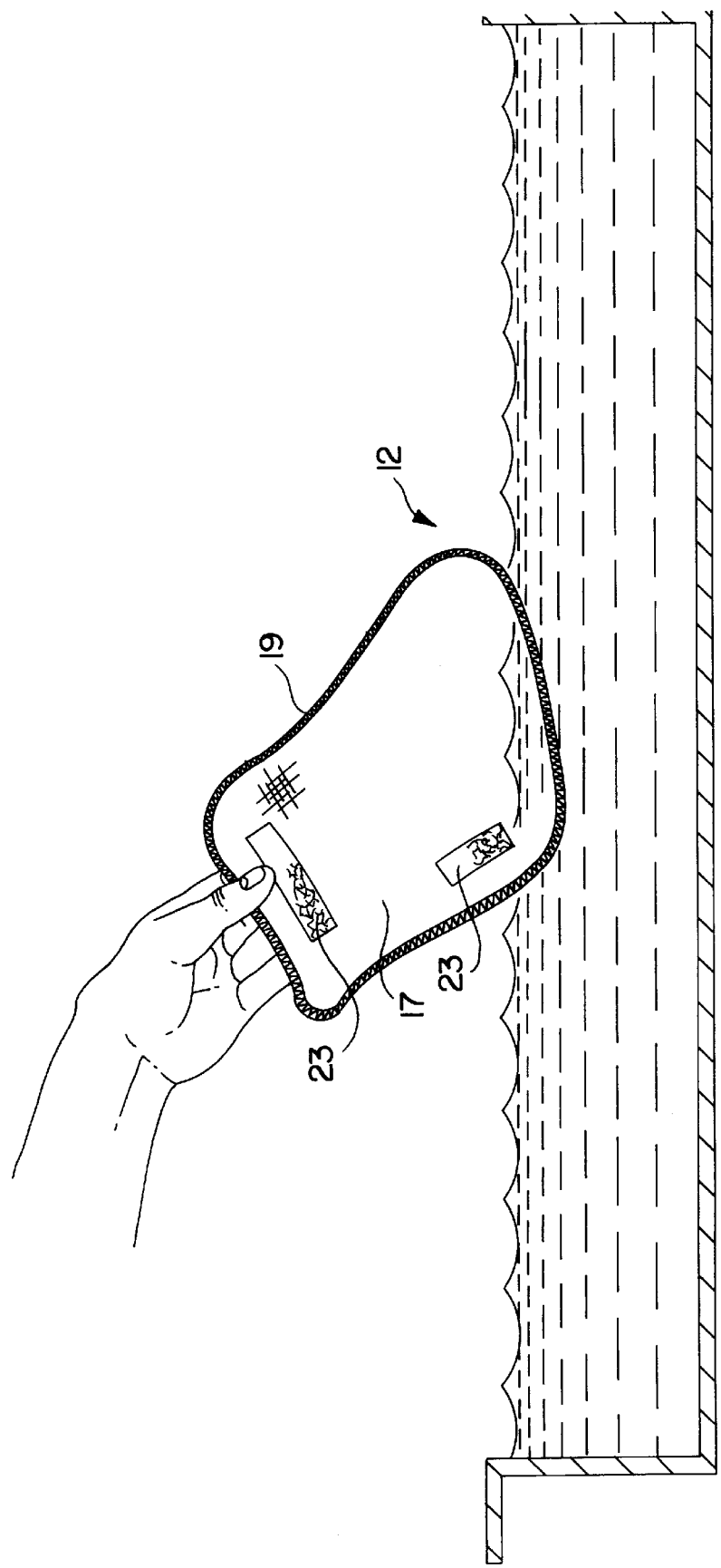
FIG. 2 is a perspective view of showing wetting of the shin guard prior to application to the shin.

As shown in FIG. 1, the pouch 11 is opened with scissors or some other sharp object, and removed from the pouch 11. As is shown in FIG. 2, the shin guard 12 is immediately dipped in water to initiate an exothermic curing reaction, which hardens the shin guard 12 within several minutes.

Figure 3:
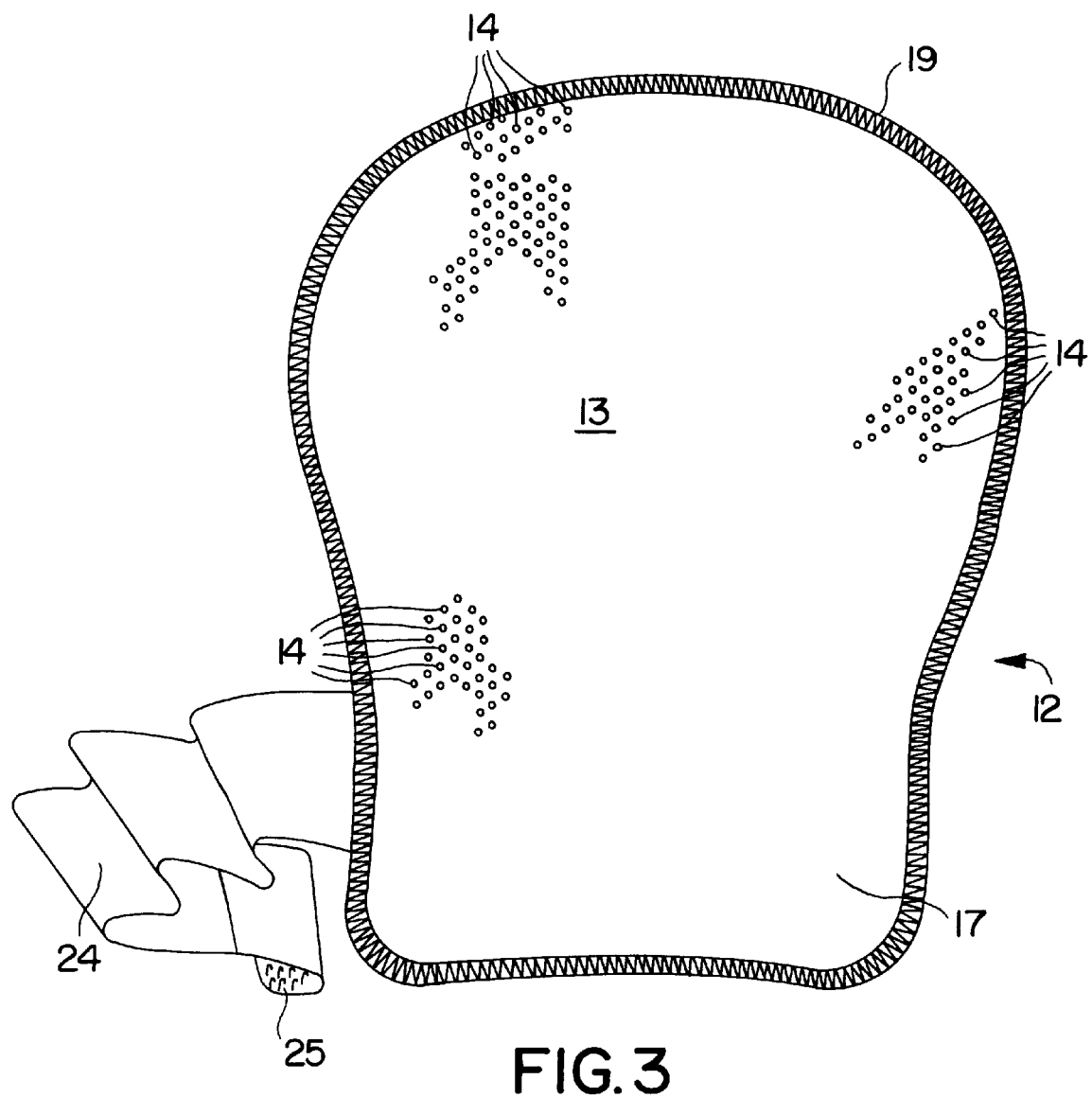
FIG. 3 is a plan view of the inner side of the shin guard.
Figure 4:
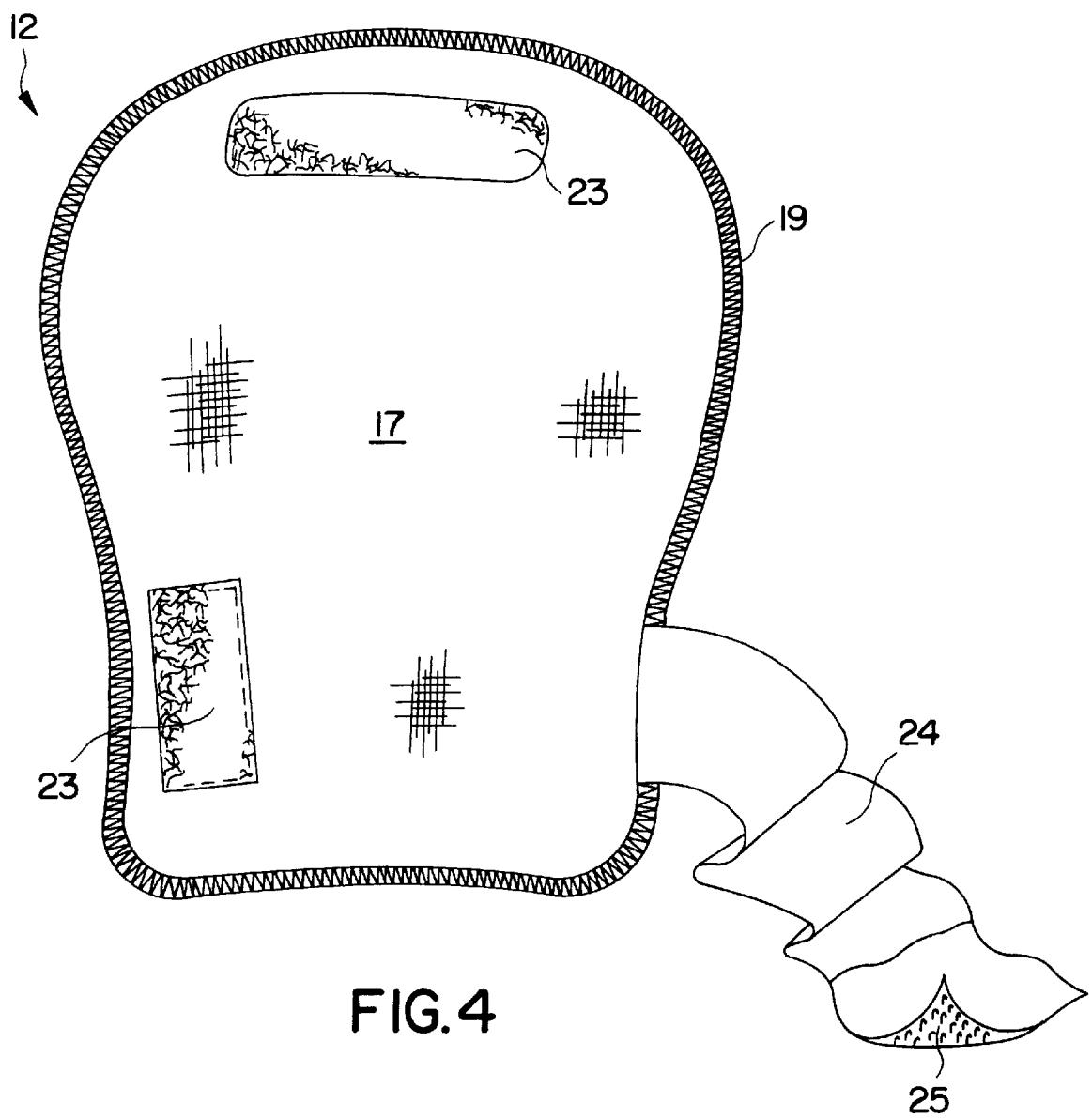
FIG. 4 is a plan view of the outer side of the shin guard shown in FIG. 2.
Figure 5:
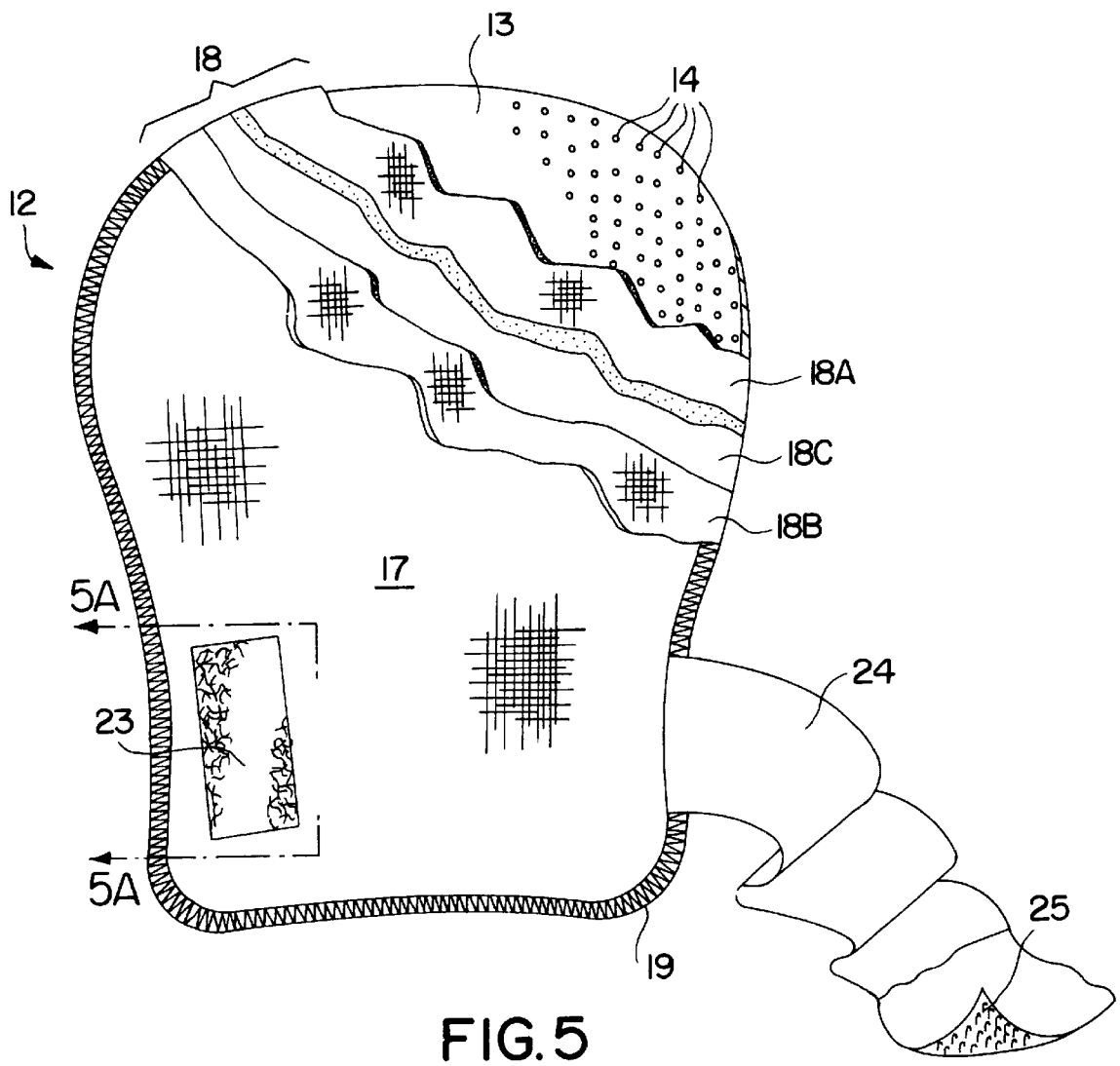
FIG. 5 is a fragmentary view with parts broken away of the shin guard shown in FIGS. 1–4.
Figure 5A:
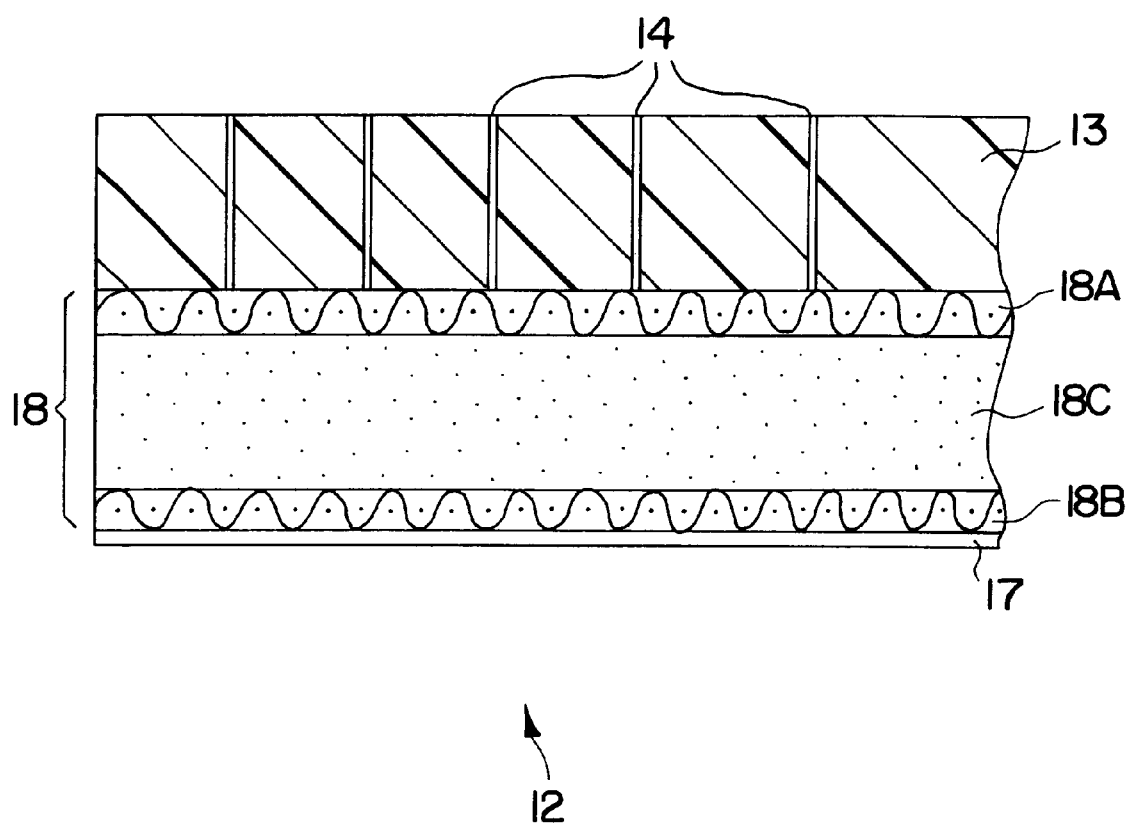
FIG. 5A is a cross-section taken through lines 5A—5A of FIG. 5.

The shin guard 12 is illustrated in further detail in FIGS. 3 through 5.

As is best shown in FIG. 3, shin guard 12 includes a cover which includes protective pad 13 on the side to be placed next to the leg, which is preferably a laminated 0.32 cm (0.125 in) 1.8 kg. (four lb.), EVA (ethylene vinyl acetate) foam. Holes 14 may be provided for ventilation. The pad 13 provides a comfortable surface next to the skin, under socks or a uniform, depending on the use. The EVA foam is flexible enough to bend easily with the other components of the shin guard 12, particularly during fitting.

Referring now to FIG. 4, the outer side of the shin guard 12 is shown. The outer side of the shin guard 12 includes a cover of a fabric 17, which may be any suitable woven or knitted material, for example, a product known as Tietex. The pad 13 and cover fabric 17 enclose a substrate 18. The pad 13, substrate 18 and cover fabric 17 are formed into a unit by means of over-edge or serging stitches 19, which extend around the perimeter of the shin guard 12.

Referring now to FIG. 5, substrate 18 is preferably formed of first and second fiberglass fabric sheets 18A and 18B, and a low density core 18C sandwiched between the fiberglass sheets 18A and 18B. The fiberglass sheets 18A, 18B and the core 18C are impregnated or coated with a moisture-curable resin which hardens upon curing to form a rigid structure which retains the shape of shin to which it is molded while still flexible.

The fiberglass preferred for the sheets 18A and 18B is S-fiberglass. S-fiberglass is 30 percent stronger, 15 percent stiffer and significantly tougher than typical E-fiberglass. The particular S-fiberglass used is a single thickness, 6580 plain weave, industrial fiberglass fabric made by Clark-Schwebel. Other fiberglass constructions may be suitable, including other woven and knitted constructions. Type 6580 S-fiberglass fabric has 29 warp ends and 28 filling ends per cm. (73 warp ends and 70 filling ends per in.), a weight of 189.2 g/m$^2$ (5.58 oz/yd$^2$) and a breaking strength of 17 nm (147 lbs/in) (warp) and 17 nm (145 lbs/in) (filling). Type 6580 S-fiberglass fabric is 0.0160 cm. (0.0063 in.) thick. Type 6580 S-fiberglass has an ultimate tensile strength of 37.9 ksi and an elastic modulus of 2026.8. These characteristics make this particular fiberglass an ideal choice.

Other fabrics which may be suitable for the sheets include fabrics made of a composition of aluminum oxide, silicone oxide, and boron oxide (sold under the trademark Nextel 440 by Thermostatic Industries, Inc.); silica-based fabrics and high modulus fabrics sold under the DuPont trademark "Kevlar," carbon filter and graphite.

The particular substrate 18C illustrated in this application is a single thickness sheet of random laid non-continuous polyester non-woven fabric incorporating a styrene-soluble binder filled 60 percent by volume with plastic microspheres. The product is sold under the trademark "Firet Coremate XM." This product is available in 2 mm (0.0787 in.), 3 mm (0.1181 in.), and 4 mm (0.1575 in.) thicknesses. The 2 mm (0.08 in.) thickness has been found suitable, and weighs 91.55–108.5 g/m$^2$ (2.7–3.2 oz/yd$^2$), has a cured specific gravity of 496.6–592.7 kg/m$^3$ (31.0–37.0 lb./ft$^3$), and a resin consumption of 3.1–3.3 kg/m$^3$ (3.1–3.3 oz/ft$^3$). As used in this application, the term "lightweight" and "low density" each refers to a product having values in relation to thickness within the general ranges set out above. For example, a shin guard made in accordance with the principles set out in this application weighs in the range of 50–100 g (1.8–3.6 oz.)

Other "Firet Coremat" grades, such as Firet Coremat XX and Firet Coremat XW may also be suitable. These grades are filled with plastic microspheres to 50 percent by volume. Other products which may be suitable include a low density, non-woven continuous strand fabric such as BaltekMat T-2000. This product has characteristics which are generally similar to Firet Coremat.

The moisture-curable resin used to impregnate or coat the substrate 18 is a polyisocyanate as described in full in U.S. Pat. No. 4,770,299. This reactive system remains stable when maintained in substantially moisture-free conditions, such as in the moisture-impervious pouch 11, but hardens upon exposure to sufficient moisture to form a rigid, self-supporting structure. Set out below is a typical formulation suitable for practice of the present invention:

TABLE 1

Typical Formulation:

| Isonate↓ 143L | or | | |
|---|---|---|---|
| Mondur↓ CD | or | polyisocyanate | 50.0% |
| Rubinate↓ XI168 | | | |
| Pluracol↓ P1010 | | polyol | 46.6% |
| DC-200 Silicone | | defoaming agent | 0.30% |
| Benzoyl Chloride | | stabilizer | 0.10% |
| Thancat↓ DM-70 | | catalyst | 3.0% |
| | | | 100% |

A complete discussion of the parameters of the reactive system, the manners of production, and the variables which apply are found in U.S. Pat. No. 4,411,262.

The polyisocyanate resin is characterized by being in a viscous, liquid unhardened state so long as the resin is not exposed to-moisture. This permits substrate 18 and any flexible structure bonded to substrate 18 to remain flexible and moldable so long as the resin is not exposed to moisture, and for a relatively short period of time after exposure to moisture. The curing time can be controlled to some extent by the quantity of water to which the resin is exposed. For example, exposure to water by dipping will result in quite rapid curing, while merely allowing the resin to be exposed to air will cause long curing times proportional to the amount of moisture, i.e., the humidity, in the air to which it is exposed.

A patch 23 of loop material is secured to the shin guard 12 as shown in FIGS. 3–5 and is optionally available to secure the shin guard 12 to the leg. This is accomplished by means of an elastic strap 24 attached by sewing stitches to one side edge of the shin guard 12. The strap 24 includes a patch 25 of complementary hook material on one end thereof which releasably attaches to the loop material on the patch 23, as shown in FIGS. 7 and 8.

Figure 6:
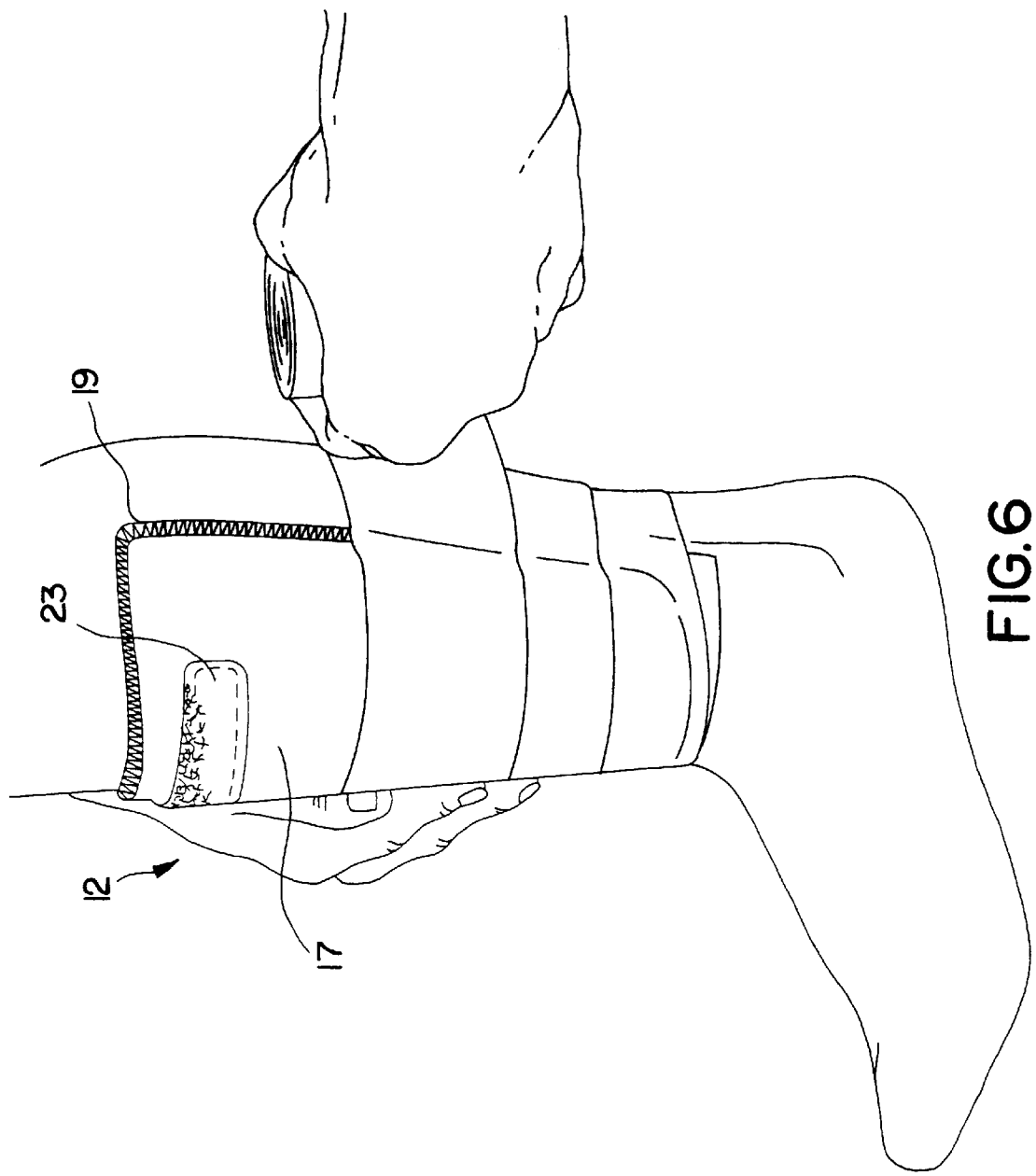
FIG. 6 is a perspective view showing the shin guard being molded to the shin and wrapped for curing.

Custom fitting of the body protective guard, as described above, will now be explained with reference to FIGS. 6 through 9 with particular reference to the shin guard 12 illustrated and described above. As removed from the pouch 11, the shin guard 12 is soft and flexible. The shin guard 12 is then moistened by dipping in water as is shown in FIG. 2. While wet but still flexible, shin guard 12 is immediately applied to the shin as shown in FIG. 6. Since curing of the resin in the substrate 18 begins immediately, the wearer must be available when the shin guard 12 is removed from the pouch 11. The shin guard 12 is then held firmly in position on the shin by over-wrapping the shin guard 12 with an elastic bandage. Ordinarily, the resin will completely cure and the shin guard 12 will be permanently molded into the exact shape desired in ten minutes or less. Resins of the type used to produce the molded shin guard 12 as described above cure quickly and result in a very rigid and strong, but extremely lightweight structure. The rigidity and strength of the resulting structure provide excellent protection against injury, while protecting previous injuries or wounds from further impact-induced damage.

Figure 7:
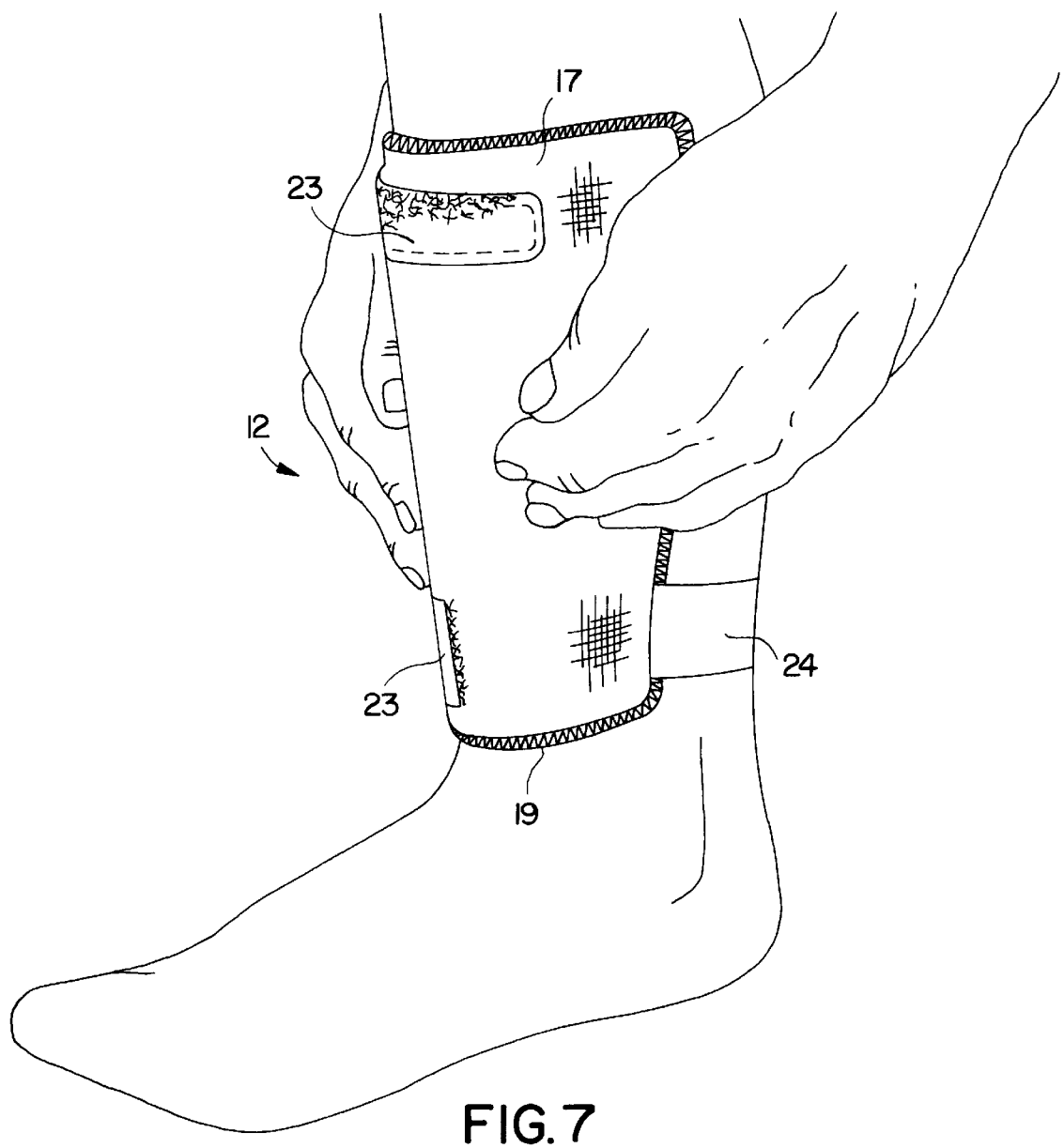
FIG. 7 is a perspective view showing the shin guard being placed on the shin for wear.
Figure 8:
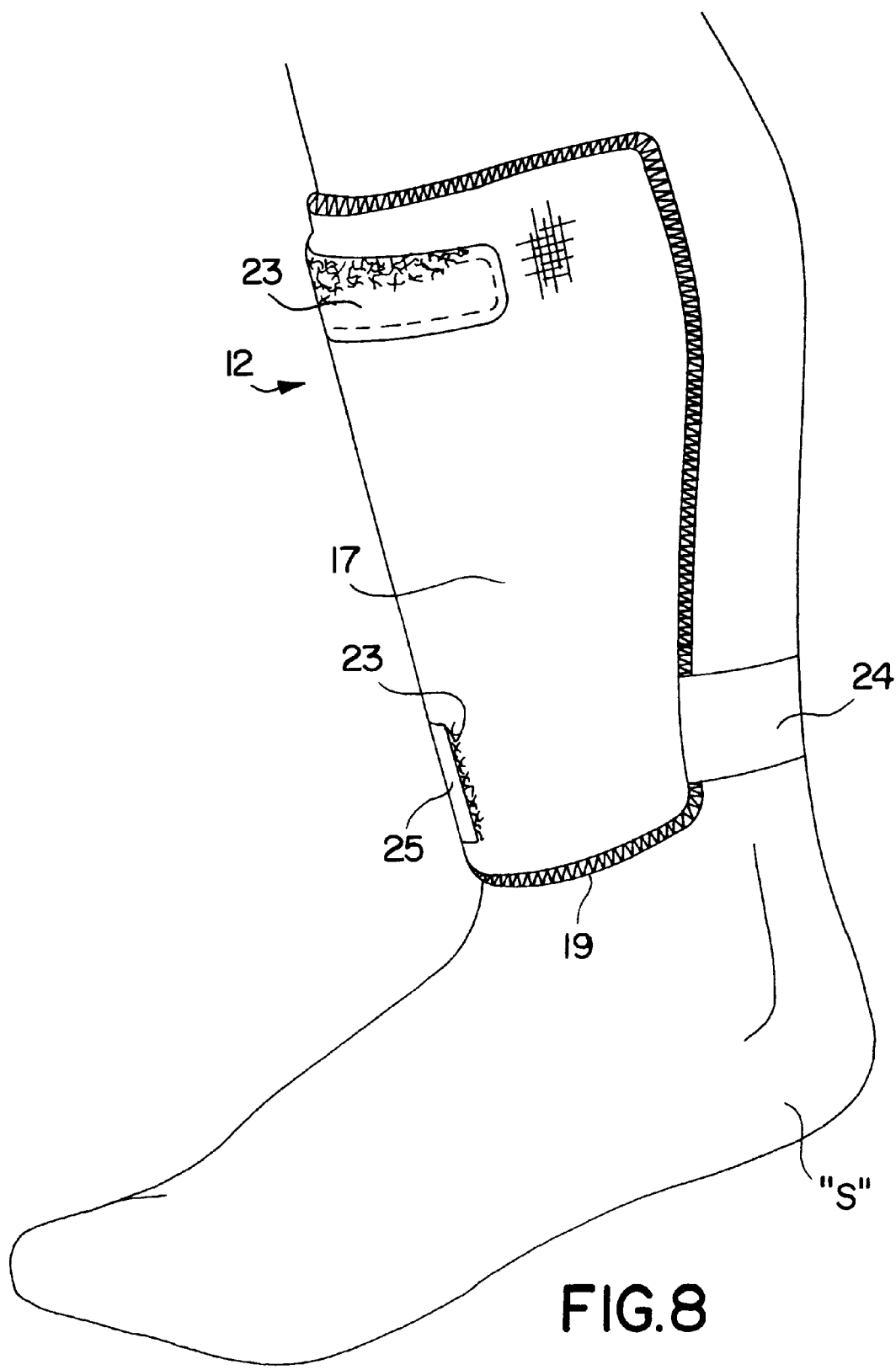
FIG. 8 shows the shin guard properly placed on the shin.
Figure 9:
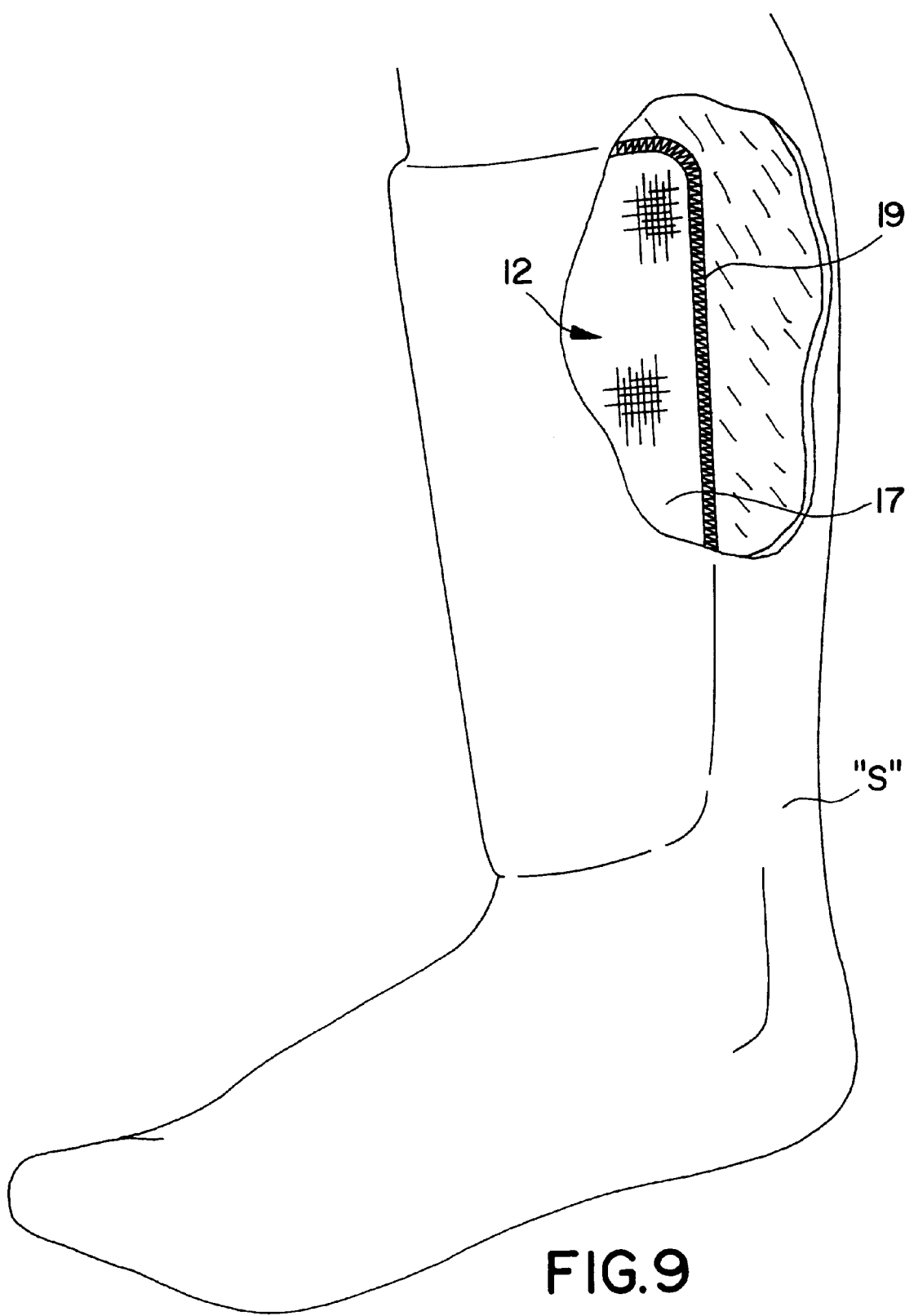
FIG. 9 shows an alternative embodiment of a shin guard being held in place under a sock.

As is shown in FIGS. 7 and 8, the shin guard 12 can be worn directly next to the skin. The shin guard 12 can also be worn under, for example, a soccer game sock "S", as shown in FIG. 9. Since the shin guard 12 is molded directly next to the skin, the fit is virtually perfect, and fits so well that straps or belts may not be needed. The shin guard 12 can be held in place merely by the sock and the adherence of the shin guard 12 to the corresponding shape of the shin. In such cases, the elastic strap 25 can be removed. Of course, shin guards otherwise made in accordance with this application can be fabricated without any means of attaching the shin guard to the leg, and instead by held in place by a sock, an elastic band compression sleeve or other over-wrap.

Analysis has shown the superiority of the shin guard disclosed in this application. Relative strength and stiffness testing was carried out to determine the degree to which the load was distributed over the area covered by the shin guard. This is a function of stiffness. To determine stiffness the guard was flat-plate loaded in a three-point bending apparatus to form a beam 22 cm. by 13.5 cm (8.7 in. by 5.3 in.) The load was 250 n (56.2 lbf.)—an arbitrary load chosen to determine relative stiffness. The comparison shows that a Parker OSi shin guard ("Parker") had a deflection of 2.07 cm (0.82 in.), while the shin guard with the Firet Coremat ("Coreguard") core has a deflection of only 0.0106 cm (0.0042 in.)

The following tables disclose the results of tests comparing weight, thickness, impact dispersion.

TABLE 2
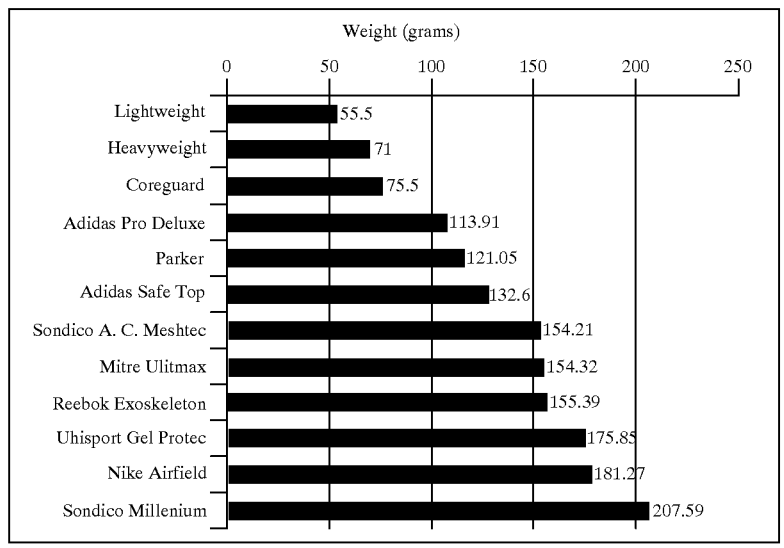
TABLE 3
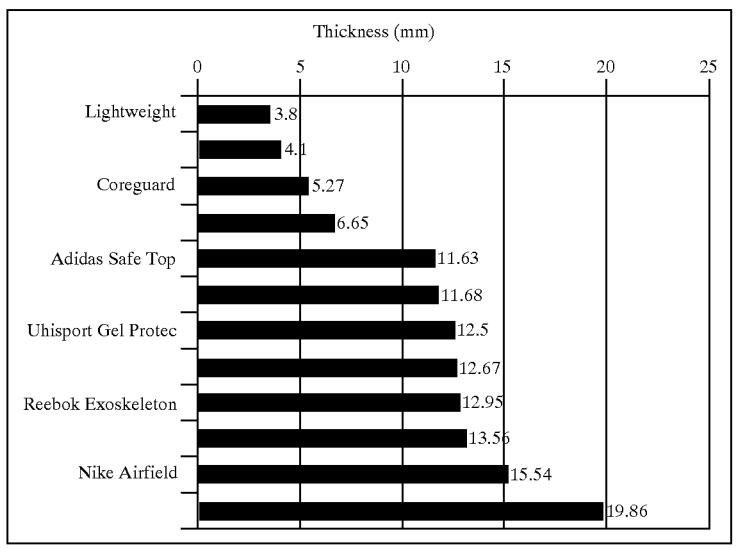

TABLE 4
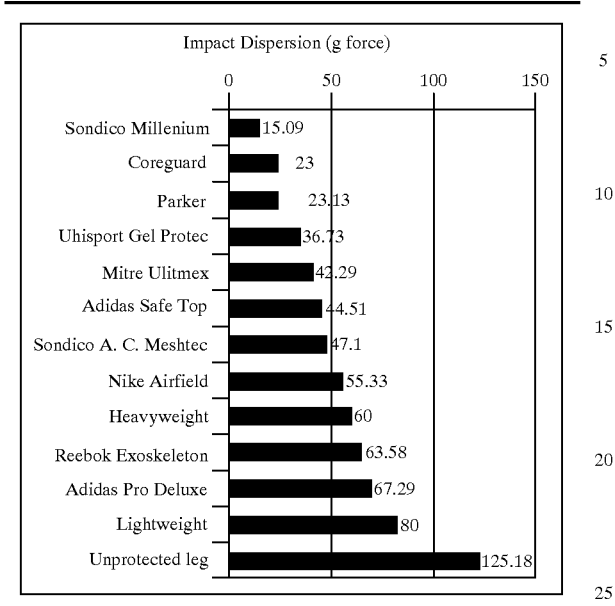
Overall performance was determined in two different ways. First, in Table 5 the weight, thickness and the impact dispersion ×2 were summed, as shown below:
TABLE 5
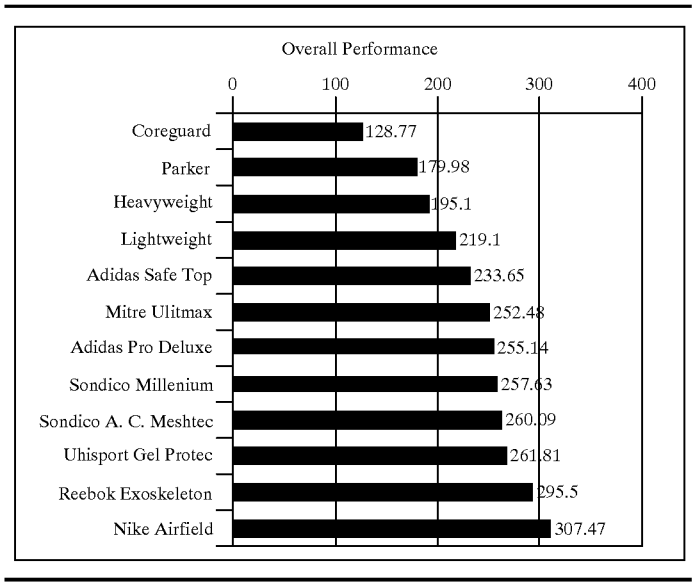

Alternatively, the data was "normalized" by averaging all of the samples in one category and dividing the individual criteria by that average. For example, if the average weight of all of the guards is 10 g (0.3527 oz.) and a particular guard has a weight of 20 g (0.7055 oz.), then the normalized factor that the guard would be "2." Done this way, the data does not assign false weight to a product because it excels in one particular category. The result achieved by normalizing the data is shown in Table 6.

TABLE 6

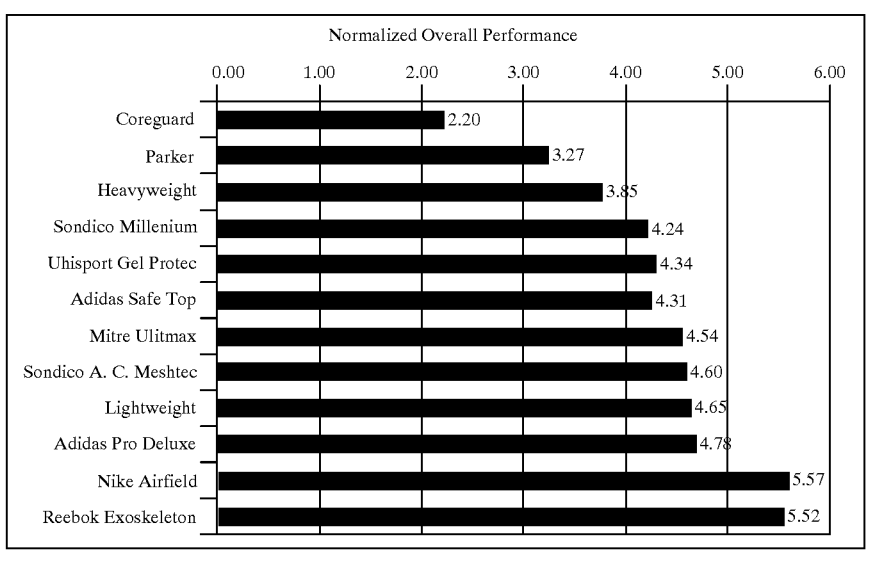

Tables 5 and 6 clearly demonstrate that a shin guard made in accordance with the invention offers superior performance characteristics, in that it is stiffer, stronger and thinner that any other guard tested.

An athletic body protective guard such as a shin guard for being molded onto a body part to be protected is described above. Various details of the invention may be changed without departing from its scope. Furthermore, the foregoing description of the preferred embodiment of the invention and the best mode for practicing the invention are provided for the purpose of illustration only and not for the purpose of limitation—the invention being defined by the claims.

What is claimed is:

1. A custom-fitted athletic body protective product, comprising:
   (a) a storage package formed of moisture-impervious material and scalable to prevent entry of moisture;
   (b) a flexible protective guard positioned in said storage package and scaled therein against entry of moisture, and for being custom-formed to the shape of a body part to be protected while flexible and upon hardening providing a rigid, supporting custom fit to the body part, said protective guard comprising;
      (i) a core defining first and second major surfaces and having a cured density of 31–37 lb/ft$^3$;
      (ii) first and second sheets positioned in overlying relation on respective first and second major surfaces of the core, said core and said first and second overlying sheet materials collectively defining a laminated substrate;
      (iii) a reactive system impregnated into or coated onto said substrate, said system remaining stable when maintained in substantially moisture-free conditions and hardening upon exposure to sufficient moisture to form a rigid, self supporting structure of the substrate; and
      (iv) a cover enclosing the substrate.

2. A body protective product according to claim 1, wherein said cover includes a flexible protective pad positioned on one side of the substrate along its length to provide a cushioning barrier between the hardened substrate and the protected body part.

3. A body protective product according to claim 2, wherein said cover includes a fabric material enclosing the substrate on a side opposite the flexible protective pad.

4. A body protective product according to claim 2, wherein said flexible protective pad comprises foam.

5. A body protective product according to claim 1, wherein said core comprises a random non-continuous polyester nonwoven fabric.

6. A body protective product according to claim 1, wherein said core comprises a random non-continuous polyester nonwoven fabric having a filler comprising microspheres.

7. A body protective product according to claim 1, wherein said core comprises a random non-continuous polyester nonwoven fabric filled with microspheres at least 50 percent by volume.

8. A body protective product according to claim 1, wherein said core comprises a random non-continuous polyester nonwoven fabric filled with microspheres at least 60 percent by volume.

9. A body protective product according to claim 6, 7 or 8, wherein said microspheres are plastic, and said core includes a styrene-soluble binder.

10. A body protective product according to claim 5, 6, 7 or 8, wherein said core is between 2 and 3 mm thick.

11. A body protective product according to claim 1, wherein said core comprises a low density, nonwoven, continuous strand fabric.

12. A custom-fitted athletic body protective guard, comprising:

a flexible protective guard and for being custom-formed to the shape of a body part to be protected while flexible and upon hardening providing a rigid, supporting custom fit to the body part, said protective guard comprising;

(a) a core defining first and second major surfaces and having a cured density of 31–37 lb/ft$^3$;

(b) first and second sheets positioned in overlying relation on respective first and second major surfaces of the core, said core and said first and second overlying sheet materials collectively defining a laminated substrate;

(c) a reactive system impregnated into or coated onto said substrate, said system remaining stable when maintained in substantially moisture-free conditions and hardening upon exposure to sufficient moisture to form a rigid, self supporting structure of the substrate; and (d) a cover enclosing the substrate.

13. A body protective guard according to claim 12, wherein said cover includes a flexible protective pad positioned on one side of the substrate along its length to provide a cushioning barrier between the hardened substrate and the protected body part.

14. A body protective guard according to claim 13, wherein said cover includes a fabric material enclosing the substrate on a side opposite the flexible protective pad.

15. A body protective guard according to claim 14, wherein said core comprises a random non-continuous polyester nonwoven fabric filled with microspheres at least 50 percent by volume.

16. A body protective guard according to claim 14, wherein said core comprises a random non-continuous polyester nonwoven fabric filled with microspheres at least 60 percent by volume.

17. A body protective guard according to claim 15 or 16, wherein said microspheres are plastic, and said core includes a styrene-soluble binder.

18. A body protective guard according to claim 15 or 16, wherein said core is between 2 and 3 mm thick.

19. A body protective guard according to claim 14, wherein said core comprises a low density, nonwoven, continuous strand fabric.

20. A body protective guard according to claim 13, wherein said flexible protective pad comprises foam.

21. A body protective guard according to claim 12, wherein said core comprises a random non-continuous polyester nonwoven fabric.

22. A body protective guard according to claim 12, wherein said core comprises a random non-continuous polyester nonwoven fabric having a filler comprising microspheres.

23. A custom-fitted protective shinguard, comprising:

(a) a storage package formed of moisture-impervious material and sealable to prevent entry of moisture;

(b) a flexible protective shinguard positioned in said storage package and sealed therein against entry of moisture, and for being custom-formed to the shin to be protected while flexible and upon hardening providing a rigid, supporting custom fit to the shin, said shin comprising;

(i) a core defining first and second major surfaces and having a cured density of 31–37 lb/ft$^3$;

(ii) first and second sheets positioned in overlying relation on respective first and second major surfaces of the core, said core and said first and second overlying sheet materials collectively defining a laminated substrate;

(iii) a reactive system impregnated into or coated onto said substrate, said system remaining stable when maintained in substantially moisture-free conditions and hardening upon exposure to sufficient moisture to form a rigid, self supporting structure of the substrate; and (iv) a cover enclosing the substrate.

24. A shinguard according to claim 23, wherein said cover includes a flexible protective pad positioned on one side of the substrate along its length to provide a cushioning barrier between the hardened substrate and the protected body part.

25. A shinguard according to claim 23, wherein said cover includes a fabric material enclosing the substrate on a side opposite the flexible protective pad.

26. A body protective product according to claim 23, wherein said core comprises a random non-continuous polyester nonwoven fabric filled with microspheres at least 50 percent by volume.

27. A substrate structure for a custom-fitted athletic body protective product, comprising:

(a) a storage package formed of moisture-impervious material and sealable to prevent entry of moisture;

(b) a substrate structure for being packaged in a moisture-impervious storage package and sealed therein against entry of moisture, and for being custom-formed to the shape of a body part to be protected while flexible and upon hardening providing a rigid, supporting custom fit to the body part, said substrate structure comprising;

(i) a core defining first and second major surfaces, said core including a random laid, non-continuous polyester nonwoven fabric filled at least 50% by volume with microspheres and having a cured density of 31–37 lb/ft$^3$;

(ii) at least one sheet positioned in overlying relation on a respective one of the first and second major surfaces of the core, said core and said at least one sheet collectively defining a laminated substrate;

(iii) a reactive system impregnated into or coated onto said substrate, said system remaining stable when maintained in substantially moisture-free conditions and hardening upon exposure to sufficient moisture to form a rigid, self supporting structure of the substrate.

28. A body protective product according to claim 27, and including a cover which comprises a flexible protective pad positioned on one side of the substrate along its length to provide a cushioning barrier between the hardened substrate and the protected body part.

29. A body protective product according to claim 28, wherein said cover includes a fabric material enclosing the substrate on a side opposite the flexible protective pad.

30. A body protective product according to claim 27, wherein said core comprises a random non-continuous polyester nonwoven fabric.

* * * * *